United States Patent [19]

Jacobs et al.

[11] Patent Number: 5,616,027
[45] Date of Patent: Apr. 1, 1997

[54] CUSTOM DENTAL TRAY

[76] Inventors: Allison J. Jacobs, 10795 Skinner Rd. N. E., Bainbridge Island, Wash. 98110; Scott Jacobs, 12105 W. Cedar Ave., Lakewook, Colo. 80228

[21] Appl. No.: 630,067

[22] Filed: Apr. 15, 1996

Related U.S. Application Data

[63] Continuation-in-part of Ser. No. 423,895, Apr. 18, 1995, Pat. No. 5,562,449.

[51] Int. Cl.⁶ ......................................... A61C 9/00
[52] U.S. Cl. ........................... 433/37; 433/48; 433/214; 433/71
[58] Field of Search ..................... 433/37, 48, 214, 433/71; 128/861, 862

[56] References Cited

U.S. PATENT DOCUMENTS

| | | | |
|---|---|---|---|
| 4,567,236 | 1/1986 | Goldwasser et al. | 525/127 |
| 5,051,476 | 9/1991 | Uji et al. | 525/186 |
| 5,415,544 | 5/1995 | Oxman et al. | 433/48 |
| 5,503,552 | 4/1996 | Diesso | 433/37 |

*Primary Examiner*—Nicholas D. Lucchesi
*Attorney, Agent, or Firm*—John S. Munday; Stephen G. Stanton

[57] ABSTRACT

A dual dental tray assembly is provided which includes a pliable resilient outer dental tray using a pre-formed thin inner tray of thermoplastic material that nests inside the pliable outer tray. The two are heated to between 145°–160° F. During this time the inner tray is more formable, allowing for the inner tray to be accurately formed over the patient's teeth. The outer tray also prolongs the time during which the inner tray is moldable. The outer tray also operates as a seal with the gums to create a better vacuum created by the patient's sucking. Thus, the inner tray, once formed and cooled, becomes hard and flexible again and provides a thin hard dental tray as accurate as dental trays produced by dentists in their labs on models. The thinner, hard dental tray can then be used for dental treatments including bleaching, fluoride applications, and other dental operations, including provisional crowns and other dental work. The outer tray is usable for fluoride gel treatments.

15 Claims, 2 Drawing Sheets

CUSTOM DENTAL TRAY

This application is a continuation-in-part of Ser. No. 08/423,895, filed Apr. 18, 1995, now U.S. Pat. No. 5,562,449.

FIELD OF THE INVENTION

The present invention relates to making a thin, hard, flexible dental tray customized to an individual patient's teeth, without the necessity of a professional's service, and the method to customize the dental tray. The invention used dual trays. The inner tray is the customized tray. The outer tray supports the inner tray during forming. Also after the process, the outer tray is available for other dental procedures.

BACKGROUND OF THE INVENTION

Dental trays are receptacles that are used to carry a medicine or dental hygiene materials, such as bleaching agents or fluoride application, and apply them to the teeth. It confines the material next to the teeth during the application. The thin dental tray of this invention is also suitable for use in creating provisional crowns. Because of its thinness, hardness and the accuracy of the impression it takes, it is equal to more expensive custom trays made over gypsum molds and models.

There are two types of dental trays: stock and customized. Stock trays are pre-fabricated into a variety of standard sizes. They are used only for preliminary procedures and to produce impressions for casting as an interim step to creating more accurate dental trays and models of teeth. Custom trays are made by a dentist or technician by molding a material over a gypsum model of the patient's teeth. In order to get the gypsum model, a preliminary impression is made from the patient's teeth. The model requires at least one dental visit and requires a laboratory to construct the gypsum model.

Once the model is made, the customized dental tray is formed by the dentist or lab according to the limitations of the materials to be used for the tray. If the tray is made of shellac or thermoplastic sheets, the tray may be formed in a vacuum forming machine or other machine which exerts pressure. The sheets are placed in a soft state over the model and pressure is applied while the material sets.

This method requires additional work to finish the tray by removing excess material and doing a final fit of the patient, requiring at least one more visit to the dentist. The result is a customized tray, but at a large cost of time and professional service. U.S. Pat. No. 4,401,616 is an example of this method wherein the material is a thermoplastic such as Polyform. Similarly, U.S. Pat. No. 4,569,342 discloses another thermoplastic, methyl methacrylate, that is heated and formed over a gypsum cast. Both require trimming.

Another variation of this method is described in U.S. Pat. No. 5,112,225, where polycaprolactone polymer is used to make a dental tray, again using a gypsum model. The polycaprolactone polymer is then formed over the teeth by the dentist or technician.

In each of these prior methods, the customized dental tray depends upon a model first created from an impression, after an office visit and with the aid of a professional. The final tray then is made after another visit and additional time with a professional. The time and expense of such a tray can be very great. The majority of the preliminary work, such as the initial impression, the model, and the interim products, is not usable for any other patient. If the patient's teeth structure changes, even the patient cannot make use of these products.

The invention disclosed in U.S. Pat. No. 5,076,791, uses ethylene vinyl-acetate and creates a customized dental tray without the necessity of a gypsum model. The resultant tray is thicker than the thin tray of this invention, which may cause discomfort. Additionally, it is not hard at normal temperatures, as is the thin inner tray of this invention.

This invention addresses these problems and creates a hard, thin dental tray, suitable for many types of dental and at home procedures and uses. The thin inner tray is customizable to the same accuracy as more expensive custom trays created on a model, but at a fraction of the cost in time, professional expertise or equipment. The outer tray can be used separately for fluoride gel applications. The thin dental trays can be customized and molded in the home or outside of a dental office. These dental trays can be used in third world countries or in rural areas.

It is another object of the present invention to provide a method for making a hard, flexible custom dental tray without the necessity of intermediate models, trays or special equipment or expertise.

INFORMATION DISCLOSURE

The following information is provided in compliance with the inventor's duty to disclose all pertinent information which is relevant to the examination of the subject application. The listed patents are known to the applicant and are believed to be pertinent. It is not to be assumed that this list is all inclusive of any search which may have been performed for or by the applicant. In addition, it is possible that other patents may have been considered by the applicant but only those items which are listed are believed to be pertinent and are of concern with respect to the examination of this patent.

The Greenberg patent (U.S. Pat. No. 3,527,219) is an application for the treatment of teeth and/or gums wherein two materials are glued together and used to form a single dental tray unit for use as an applicator for fluorides or other medications. The dental tray unit is comprised of a liquid impermeable material that is injection molded into a horseshoe-shape with a channel cross-section. The inner material is a foam material medicine applicator that lines the inner surface of the channel of the tray material and is attached with adhesive. The tray material or shell comes in various sizes but does not conform or mold itself to the shape of a given patient's teeth. The inner foam layer does, in a resilient or sponge fashion, conform to the teeth. In its open-cell foam configuration, the inner layer is discarded more frequently than in a closed-cell foam configuration. In either the closed- or open-cell configuration, pressure must be exerted to keep the inner layer in contact with the teeth. In the closed cell, greater pressure is needed.

The Monaghan patent (U.S. Pat. No. 3,379,193) shows a use of a plastic material to form upper and lower teeth covers to be used to apply medicines. The covers are shaped to the teeth of the patient by the patient's forming a tube of thermoplastic material over the teeth while in a softened state. This material is initially softened by heating in boiling water. The patient bites the softened material. The material is then cooled to a resilient state, retaining the impressions of the teeth. Medicine is then applied by the teeth covers and sued by the patient over the appropriate teeth.

The Porter patent (U.S. Pat. No. 3,688,406) discloses a pliable carrier (such as tin foil) in a horseshoe shape. The carrier is flat initially but formed into a channel form around the upper or lower teeth during initial use by the patient. Inside the carrier is an adhesive surface. Medicine is applied to the adhesive surface to, in turn, be applied to the teeth during use.

The Jacobs patent (U.S. Pat. No. 3,312,218) describes a mouth protector for use in sports. The mouth protector is made from a thermoplastic material that conforms to the user's mouth and cushions the user's teeth from impact. The material is initially formed into a single U-shaped channel. It is heated to a temperature higher than body temperature. While in a soft and moldable condition, it is placed in the mouth and formed by biting, sucking and pressure. At body temperature, it is shape-retaining, tough, flexible and resilient.

The Jacobs patent (U.S. Pat. No. 4,044,762) describes an improved mouth guard (U.S. Pat. No. 3,312,218) that also operates to apply medication such as fluoride while being worn.

The Madray patent (U.S. Pat. No. 5,076,791) discloses a bleaching dental tray that is formed by the wearer at home by first softening the pre-formed tray in boiling water, then placing it in the user's mouth while in a soft state and forming it to the teeth by way of finger and tongue pressure. Once cooled, the tray is then used with a bleaching agent inside the tray while being worn by the user.

The Diesso patent (U.S. Pat. No. 5,112,225) discloses a custom formed dental tray made from polycaprolactone for use in bleaching, fluoride application or in the use of impression paste or material in order to get an impression. The polycaprolactone is heated in hot water and rolled into a tube form. It is then placed and formed over a gypsum cast molding of the patient's teeth by the dentist by hand. It is allowed to cool to room temperature and harden.

SUMMARY OF THE INVENTION

The present invention is an assembly of two components, referred to as the carrier tray and the inner tray. The device assembly may be used to make a dental tray on either the upper or lower teeth. The same carrier tray may be used for both upper and lower teeth with a second inner tray being used for the second impression. The inner tray may be re-used after changes in the teeth by reheating and redoing the forming process disclosed.

The inner tray and carrier tray come in multiple sizes to allow the selection of a size that generally conforms to the size of the patient's mouth. The inner tray is principally made of a composition of polycaprolactone polymer with co-polymers and additives. The carrier tray is made of a ethylene vinyl-acetate such as Elvax 250 by DuPont.

The inner tray, at normal atmospheric temperature, is flexible yet hard, thus retaining an accurate impression of the teeth. At a temperature range of 145°–160° F., it becomes pliable and moldable to readily take an impression of the teeth or gums. The outer configuration of the inner tray is a horseshoe-shape, having an open U-shaped cross-section to generally fit over the upper or lower teeth.

The carrier tray is a thermoplastic material made from ethylene vinyl-acetate, such as Elvax 250, manufactured by DuPont. It remains flexible and resilient at, atmospheric temperature but retains its shape at temperatures in the range of 145°–160° F. The carrier tray configuration is also a horseshoe shape having an open U-shaped cross-section to general fit over the upper or lower teeth.

The carrier tray and the inner tray fit or nest together with a friction fit as the assembled device. The inner tray and carrier tray are heated together, inserted into the mouth together and are together during the forming process.

The forming process is done by submerging the assembly into water or other suitable non-solvent liquid between 145°–160° F. Both trays become sufficiently pliable after being submerged for four to ten seconds. While in this condition, the two trays, in their assembled condition, are put into the patient's mouth over the upper or lower teeth. The patient closes his or her mouth. A vacuum is created inside the device by sucking on the assembly, drawing air and water out of the assembly and teeth interface. Additional forming pressure can be applied by fingers massaging the device on the surface of the carrier tray or with the tongue.

Because of the material and the thinness of the walls of the inner tray, the inner tray will substantially lose integrity of its shape and form during the heating process and while in the temperature range of 145°–160° F. The carrier tray is necessary during the heating, handling and forming process. The carrier tray gives the inner tray mechanical support while it is in its moldable state and gives added retained heat to the assembly to allow for a reasonable time to form the impression on the inner tray.

After forming, the assembled device is taken out of the mouth and cooled, either by placing the assembly in cold water or by letting it come to room temperature. When at room temperature, the carrier tray, which is still pliable, is removed from the inter-tray which is flexible and hard. The inner tray will have an impression of the teeth desired. If additional forming is needed either immediately or later, the device may be reassembled, heated as before and formed as before. After the inner tray is formed, it can be used for lab work, such as making provisional crowns, and for application of medicine or treatment. It can easily be refitted, if needed. It can be discarded after use. The carrier tray can also be used separately for application of medicines or treatments such as fluoride gels.

In the event there are areas of the teeth that have irregularities, such that the moldable inner tray may attach to these irregularities, a blocker material, such as a suitable silicone-based elastomer, may be used in this limited area before forming. The blocker would act as a spacer to prevent the inner tray from being molded and setting in such a manner that the irregularities or fillings are captured or caught by the inner tray material.

The invention provides a thin-walled, hard yet flexible dental tray that is easily and inexpensively made without the necessities of repeat visits to a dentist or doctor, and without the necessity of sophisticated equipment or technicians. The end product is suitable for many dental and oral hygiene treatments, with the accuracy of more expensive customized trays.

DETAILED DESCRIPTION OF THE INVENTION

An important element of the invention is the use of a double tray with the two trays being of two different materials. The inner hay is easily customized. The resulting trays are separately usable for treatments. The inner tray is also usable for making provisional crowns.

Figure 1:
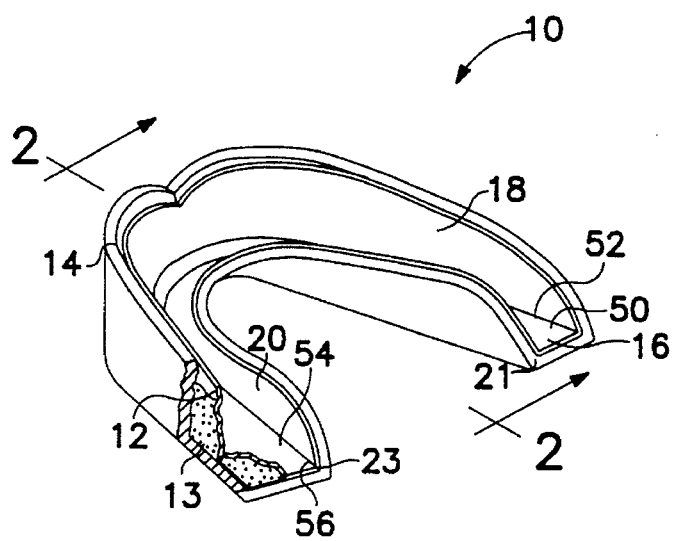
FIG. 1 is an isometric view showing the device assembly according to the present invention.
Figure 3:
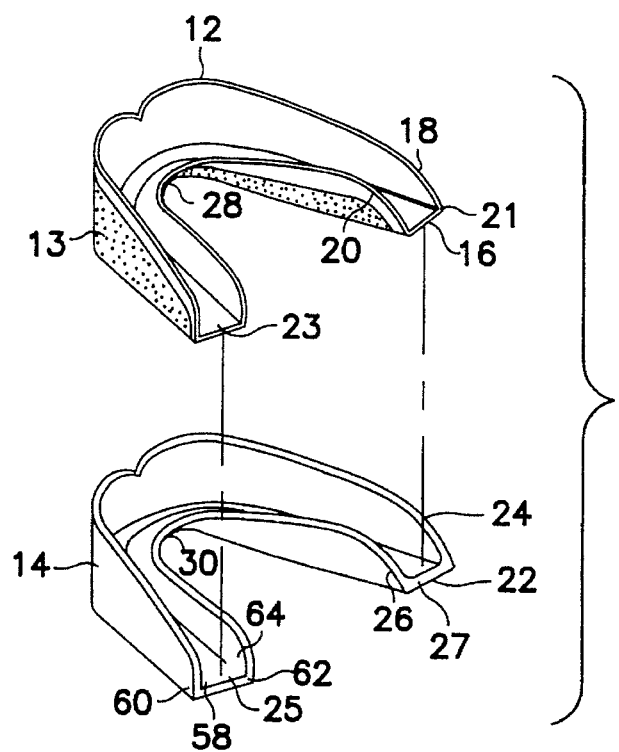
FIG. 3 is an exploded view showing the two components of the device assembly.
Figure 4:
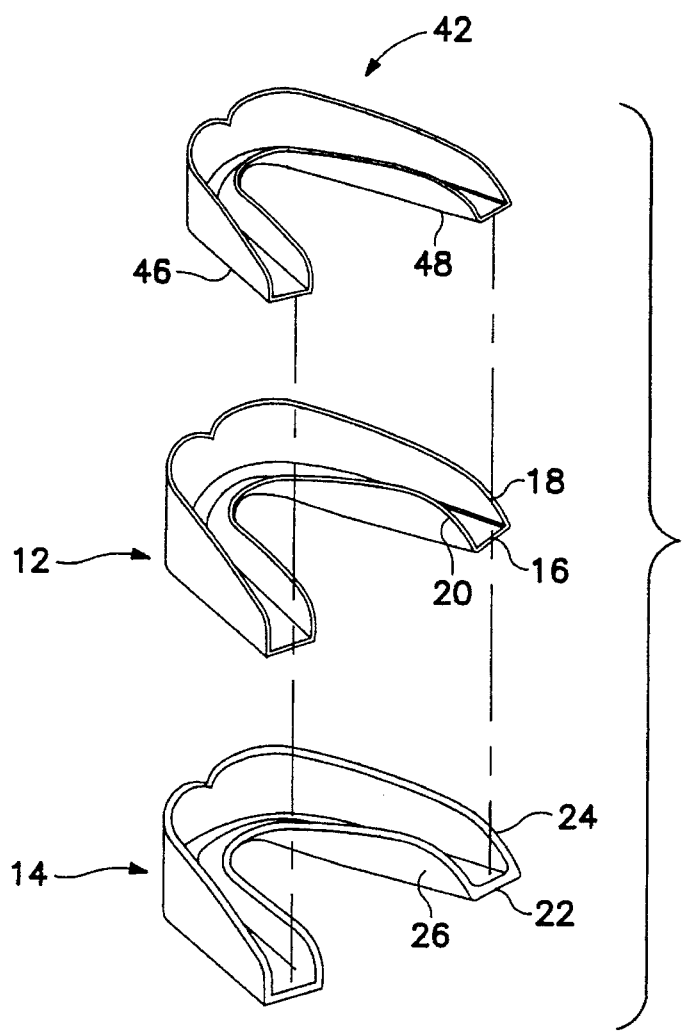
FIG. 4 is an exploded view showing an alternative embodiment of the device assembly, including a blocking layer.
Figure 5:
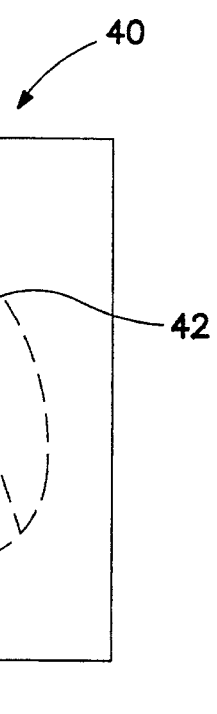
FIG. 5 is a top view of the sheet of blocker material with a pattern for the blocker layer.

FIG. 1 shows an assembled dental tray device 10 with the inner tray 12 fitted inside the carrier tray 14. FIG. 3 shows the exploded view of the assembly 10. The inner tray 12 is comprised of a bottom ball 6 in a U-shaped configuration generally in the shape of a row of teeth with an outer side wall 18 attached at the bottom surface 50 to the outer edge 52 of the bottom wall 156. The two side walls 18 and 20 and bottom wall 16 form the inner tray 12 in a horseshoe shaped configuration with a U-shaped cross-section open at the ends 21, 23.

The carrier tray 14 is similarly in a horseshoe shaped configuration with a U-shaped cross-section. It is formed by having a bottom wall 22 in a horseshoe shaped configuration, generally in the shape of a row of teeth, whose outer edge 58 is attached to the bottom surface 60 of the outer side wall 24 and whose inner edge 62 is attached to he bottom surface 64 of the inner side wall 26. The U-shaped cross-section is open at the ends 25, 27.

Figure 2:
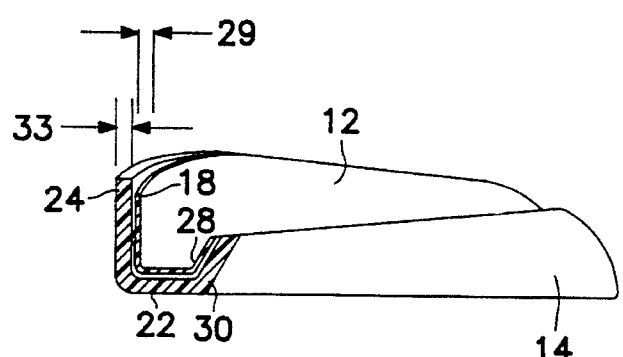
FIG. 2 is a cross-sectional view of the device assembly taken along lines A—A of FIG. 1.

The wall thickness 33 of the tray is approximately 1.5 mm (0.059 inches). The wall thickness 29 of the inner tray 12 is between 0.26 mm to 1.25 mm (0.01 inches to 0.05 inches). The thickness that seems to work well for the inner tray is 1 mm (0.04 in.). The outside wall 24 of the carrier tray 14 and the outside wall 18 of the inner tray 12 are nearly perpendicular to their respective bottom walls 22 and 16. The inner wall 20 of the inner tray 12 and the inner wall 26 of the carrier tray 14 is nearly perpendicular to the respective bottom walls 22 and 16 at the ends of the horseshoe shaped trays 12, 14 but gradually becomes an oblique angle 32 (as seen in FIG. 2) so as to accommodate the roof and palate of the mouth near the center 28 of the inner tray 12 and the center 30 of the carrier tray 14. The width of the bottom 16 at the center 28 of the inner tray 12 and the bottom 22 at the center 30 of the carrier tray 14 is narrower than the respective bottoms 16, 22 at the ends 21, 23 and 25, 28 of the respective trays. This is to allow for the differences in the radial width of normal teeth along the arch of the teeth.

The outside dimension of the cross-section of the inner tray 12 is equal to the inside dimension of the cross-section of the carrier tray 14. When assembled, the preferred embodiment requires no adhesive. The assembly will stay together during heating, handling and forming by way of friction forces.

In FIG. 2, the inner tray 12 and carrier tray 14 are shown as a cross-section. Though not to scale, the drawing does illustrate that the wall thickness 29 of the inner tray 12 is less than the thickness 33 of the carrier tray 14. FIG. 2 also illustrates the oblique angle between the inner side walls 20, 26 and the bottom walls 16, 22 at centers 28 and 30. The thinness 29 of the walls of the inner tray 12 is an important feature for the comfortable use, ease of use and successful conforming of the inner tray or use while still producing an accurate, hard, flexible tray. The thinness of the inner tray 12, because it loses the ability to maintain its shape at molding temperatures, is a problem that is resolved by the double tray assembly set forth herein. The carrier tray 14, although moldable in the temperature range of 145°–160° F., has sufficient mechanical integrity to keep the carrier tray 14 and inner tray 12 in their original shapes during heating, handling, insertion into the mouth and molding.

The height of the walls 18, 20 of the inner tray 12, when assembled with the carrier tray 14, are less than the height of the walls 24, 26 of the carrier tray 14. This is to facilitate the use of the carrier tray 14 as a sealing mechanism with the gums to help create the conforming vacuum. The higher walls 24, 26 of the carrier tray 14 will extend beyond the walls 18, 20 of the inner tray 12, to insure that the carrier tray 14, being more flexible and resilient over a wider range of temperatures due to its hardness characteristics, will make and maintain the seal with the gums necessary for the suction forming in the mouth. Additionally, due to the hardness of the inner tray 12 at atmospheric temperature because of its material composition, it is desirable that the walls 18, 20 of the inner tray 12 will not rub on the surface of the gums during wearing. Also because of the dimension 29 of the walls of the inner tray 12, they can be trimmed easily by the use of curved cuticle scissors or other similar instruments.

As described, the preferred embodiment uses the friction fit of the inner tray 12 with the carrier tray 14 to keep the dental tray assembly 10 together during heating, handling and fitting. As an alternative, a suitable, non-solvent, removable adhesive 13 may be applied between the carrier tray 14 and inner tray 12. The adhesive 13 should be selected so as not to interfere with the materials, have adhesive quality during the temperatures of heating and molding, be suitable for use in patient's mouths and have adhesive qualities such that when the inner tray 12 is set and hard, the carrier tray 14 can be peeled away from the inner tray 12 and the adhesive 13 easily removed.

The carrier tray 14 is comprised of a thermoplastic co-polymer made of a ethylene vinyl-acetate with a vinyl acetate proportion in the range of 27.2% to 28.8%, yielding a melt index of 22 to 28 decigrams/minute. A suitable product is Elvax 250 from DuPont.

The inner tray 12 is a combination of polyester resins, co-polymers, and additives made up of the following configuration: 50% to 80% by weight of polycaprolactone, an aliphatic polyester resin with a molecular weight of 40,000 to 80,000, such as Capra 650 from Solvoy-Interox; 10% to 40% by weight of ethylene vinyl-acetate co-polymer with a proportion of vinyl acetate being in the range of 24.3% to 25.7% by weight and a melt index of between 17.3 to 20.9 decigrams/minute, such as Elvax 350 by DuPont; 5% to 10% by weight of silica filler, such as Hisil 233 from PPG Industries; 0% to 1% by weight of primary antioxidant such as Igranox 1010 from Ciba Giege; and 0% to 1% by weight of secondary antioxidant such as Irgaphos 168 form Ciba Giege.

The applicant has found that the following composition is quite suitable for the purposes of the inner tray: approximately 67.19% by weight of polycaprolactone, an aliphatic polyester resin, such as Capra 650 by Solvoy-Interox, approximately 9% by weight of ethylene vinylacetate co-polymer such as Elvax 350 by DuPont, approximately 9% by weight polystyrene butadiene co-polymer such as Stereon 840A by Firestone, approximately 13% by weight of silica filler, such as Hisil 233 by PPG Industries, approximately 0.2% by weight of a primary antioxidant, such as Ingranox 1010 from Ciba Giege, and approximately 0.2% by weight of a secondary antioxidant such as Igraphos 168 from Ciba Giege.

The wall thickness of the carrier tray 14 is thicker than the inner tray 12. Because the carrier tray 14 is thicker and because of the material used, it retains more shape integrity at the temperatures used in heating the dual trays. Thus, it gives mechanical support to the inner tray 12 to retain the inner tray's 12 basic shape while being heated, handled and inserted in the mouth. Without the carrier tray 14, the inner tray 12 would be very difficult to work with and to properly insert in the mouth.

The carrier tray 14 also provides another benefit. In the heating process, both trays are heated to between 145°–160° F. During the time from removal of the dual tray assembly 10 from the hot liquid bath until it is inserted in the mouth at a temperature that is not hot enough to cause injury or be uncomfortable, very little heat will be lost, leaving the inner tray 12 in a pliable and formable condition. The forming of the inner tray 12 will be accompanied by the vacuum formed by sucking and pressure. There will be a reasonable time for forming because the tray assembly 10 of the carrier tray 14 and the inner tray 12 will have retained heat, much more than the inner tray 12 alone. Thus the carrier tray 14 will act as a heat sink for the dual trays 10 during forming, extending the period during which the inner tray 12 may be worked into a conformed impression of the teeth. The carrier tray 14 thus performs two functions. One, to give mechanical strength and body to the inner tray 12, and the second to extend the period of time that the inner tray 12 stays in a softened state.

As an alternative embodiment, the dual tray assembly may be held together during the heating and molding process by a suitable adhesive 13 as described before.

During some applications and molding of the inner tray 12, the impression obtained may be too good. In these circumstances, imperfections in the teeth, such as undercuts or edges of fillings, may be captured by the impression on the inner tray 12, creating problems in removing the inner tray 12 from the teeth. Additionally, the inner tray 12 impression may be too accurate in that when set, the tray conforms too closely to the teeth shape, leaving little room for the use of medicines or applications such as bleaching agents.

To resolve these problems, an elastomer, such as a thin silicone-based elastomer sheet 40, may be used. The sheet 40 is of a suitable thickness, such as 0.01 to 0.05 mm. The sheet 40 can be cut to the shape of the inside channel of the inner tray 12 such as the pattern 44. The cut sheet would then be folded at lines 46, 48, forming a horseshoe shaped configuration with a U-shaped cross-section. It would then be used on the inside channel or groove of the inner tray 12. After forming in the mouth, the silicone lining 42 is removed. The now formed inner tray 12 will have an impression of the teeth but will have clearance when inserted over the teeth for application of medicines equal to the thickness of the sheet used. The silicone-based elastomer insert 42 used in the application will be called a blocker. The blocker will prevent the inner tray 12 from being formed around imperfections in the dental work that would prevent removal of the inner tray 12.

In the heating and preparation of the dual dental tray assembly 10, a useful heating method is to use a common water heating apparatus such as a drip coffee maker (not shown). The water is heated to a suitable temperature and goes into the basket where the assembly 10 is placed. The basket arrangement is sterile, in that it is used only for new dual dental tray assemblies 10. When the assembly 10 is sufficiently heated, the assembly 10 is either placed in the mouth for forming or it can be placed in a container of hot water, to keep it at a suitable temperature until it is ready to use. The coffee carafe that has captured the heated water draining from the basket can be that container. Additionally, if during fitting it is determined that the dual dental trays need to be reheated, the carafe of hot water can be used without risk of contaminating the basket area. After the forming, the carafe water is discarded. The carafe can then be sterilized for new patients.

After the dual tray assembly 10 is removed from the mouth, the assembly 10 is cooled, either by placing in cold water or in the air. At cooled temperatures, the inner tray 12 will be hard and retain the shape of the teeth. The carrier tray 14 will be flexible and resilient.

Once the dual trays are cool, the blocker 42 is removed, if one was used. Then the carrier tray 14, with or without the adhesive, is peeled from the inner tray 12. Any remaining elastomer 42 or adhesive 13 is removed from the inner tray 12 and the carrier tray 14.

The inner tray is now ready for use. The carrier tray 14 may be kept by the patient for any subsequent fittings of inner trays 12 due to dental changes or need to replace the formed inner tray 12. Also, the carrier tray 14 is usable as a dental tray to apply fluoride gel, which may be necessary to desensitize the teeth after a bleaching treatment.

We claim:

1. A dual tray assembly, comprising:
   a carrier tray configured generally to conform to a patient's teeth; and
   an inner tray with a configuration which extends over the teeth that removably nests inside the carrier tray making a dual tray assembly;
   the inner tray being made of a thermoplastic compound including 50% to 80% by weight polycaprolactone and 10% to 40% by weight of ethylene vinyl-acetate.

2. The assembly of claim 1, wherein said polycaprolactone has a molecular weight ranging from 40,000 to 80,000.

3. The assembly of claim 1, wherein said ethylene vinyl-acetate has a proportion of vinyl acetate ranging from 24.3% to 25.7% by weight and a melt index between about 17.3 and 20.9 decigrams/minute.

4. The assembly of claim 1, wherein said inner tray further includes 5% to 10% by weight of a polystyrene butadiene copolymer.

5. The assembly of claim 1, wherein said inner tray further includes 1% to 15% silica filler.

6. The assembly of claim 1, wherein said carrier tray is made from ethylene vinyl-acetate.

7. A dual tray assembly, comprising:
   a carrier tray configured generally to conform to a patient's teeth; and
   an inner tray with a configuration which extends over the teeth that removably nests inside the carrier tray making a dual tray assembly;
   the inner tray being made of a thermoplastic compound including 50% to 80% by weight polycaprolactone having a molecular weight ranging from 40,000 to 80,000; and 10% to 40% by weight of ethylene vinyl-acetate having a proportion of vinyl acetate ranging from 24.3% to 25.7% by weight and a melt index between about 17.3 and 20.9 decigrams/minute; and 5% to 10% by weight of a polystyrene butadiene copolymer.

8. The assembly of claim 7, wherein said inner tray further includes 1% to 15% silica filler.

9. The assembly of claim 7, wherein said carrier tray is made from ethylene vinyl-acetate.

10. In a dual tray assembly having a carrier tray configured generally to conform to a patient's teeth; the improvement comprising:

an inner tray with a configuration which extends over the teeth that removably nests inside the carrier tray making a dual tray assembly; the inner tray being made of a thermoplastic compound including 50% to 80% by weight polycaprolactone and 10% to 40% by weight of ethylene vinyl-acetate.

11. The assembly of claim 10, wherein said polycaprolactone has a molecular weight ranging from 40,000 to 80,000.

12. The assembly of claim 10, wherein said ethylene vinyl-acetate has a proportion of vinyl acetate ranging from 24.3% to 25.7% by weight and a melt index between about 17.3 and 20.9 decigrams/minute.

13. The assembly of claim 10, wherein said inner tray further includes 5% to 10% by weight of a polystyrene butadiene copolymer.

14. The assembly of claim 10, wherein said inner tray further includes 1% to 15% silica filler.

15. The assembly of claim 10, wherein said carrier tray is made from ethylene vinyl-acetate.

* * * * *